United States Patent
Kimura et al.

(10) Patent No.: US 7,279,509 B2
(45) Date of Patent: Oct. 9, 2007

(54) ANTIBACTERIAL COMPOSITION FOR MEDICAL TOOL

(75) Inventors: Ryoji Kimura, Tokyo (JP); Hidehiro Ishizuka, Saitama (JP); Junji Shibasaki, Saitama (JP)

(73) Assignee: Adeka Corporation, Tokyo (JP)

( * ) Notice: Subject to any disclaimer, the term of this patent is extended or adjusted under 35 U.S.C. 154(b) by 548 days.

(21) Appl. No.: 10/482,873

(22) PCT Filed: Jul. 11, 2002

(86) PCT No.: PCT/JP02/07062

§ 371 (c)(1),
(2), (4) Date: Jan. 6, 2004

(87) PCT Pub. No.: WO03/006547

PCT Pub. Date: Jan. 23, 2003

(65) Prior Publication Data

US 2004/0166163 A1 Aug. 26, 2004

(30) Foreign Application Priority Data

Jul. 12, 2001 (JP) .............................. 2001-211766

(51) Int. Cl.
*C08K 5/3432* (2006.01)
*C08K 5/527* (2006.01)

(52) U.S. Cl. ......................... 523/122; 524/99; 524/136

(58) Field of Classification Search ................ 523/122; 524/99, 136
See application file for complete search history.

(56) References Cited

U.S. PATENT DOCUMENTS

| | | | | |
|---|---|---|---|---|
| 6,517,526 | B1* | 2/2003 | Tamari | 604/403 |
| 6,525,117 | B1* | 2/2003 | Burley | 524/99 |
| 2007/0100049 | A1* | 5/2007 | Ishizuka | 524/417 |

FOREIGN PATENT DOCUMENTS

| | | |
|---|---|---|
| JP | 58-001736 | 1/1983 |
| JP | 6-192227 | 7/1994 |
| JP | 07-196869 | 8/1995 |
| JP | 10-251445 | 9/1998 |
| JP | 10-251470 | 9/1998 |
| JP | 10-251526 | 9/1998 |
| JP | 10-265678 | 10/1998 |
| JP | 11-29416 | 2/1999 |
| JP | 2001-220464 | 8/2001 |

* cited by examiner

*Primary Examiner*—Tae H Yoon
(74) *Attorney, Agent, or Firm*—Young & Thompson

(57) ABSTRACT

An antibacterial composition for medical tools made of a vinyl chloride resin, which comprises a specific cyclic organic phosphoric ester compound and a specific pyrithione compound and has excellent antibacterial properties; and a medical tool made of an antibacterial vinyl chloride resin obtained by adding the antibacterial composition to a vinyl chloride resin.

15 Claims, No Drawings

ANTIBACTERIAL COMPOSITION FOR MEDICAL TOOL

TECHNICAL FIELD

The present invention relates to an antimicrobial composition for a medical tool made of a vinyl chloride resin, which comprises a specific cyclic organic phosphoric ester compound and a specific pyrithione compound and a medical tool made of an antimicrobial vinyl chloride resin having incorporated therein the antimicrobial composition.

BACKGROUND ART

In recent years, houses with less air circulation and equipped for air conditioning and heating have provided a hotbed for growth of bacteria and molds, which allows microorganisms to grow all the year. Control of bacteria or mold growth is important especially for patients who are exposed to an environment having bacteria harmful to humans and are less resistant to these bacteria with their reduced physical strength due to their diseases and for health workers who work in such an environment.

In particular, the excrement, blood, etc. from patients have high possibility of bacterial contamination. In order to secure a safe and hygienic environment, antimicrobial properties have been increasingly demanded for disposable medical supply products made of a vinyl chloride resin, such as urine bags.

In order to make these products antimicrobial, it has been practiced to add various antimicrobial agents to a vinyl chloride resin used as a raw material or to apply a synthetic resin coating containing an antimicrobial agent to the products.

It has long been known that specific metals such as silver have antimicrobial properties. The antimicrobial properties of such metals are known attributed to a trace amount of ions leached out from their surface. Known antimicrobial agents utilizing these metals include inorganic ones prepared by modifying various inorganic compounds, such as zeolite, silica gel, and hydroxyapatite, with the metals and salts of the metals with various organic acids.

These known metal-based antimicrobial agents, however, are still unsatisfactory. Besides, those using silver suffer from remarkable color change due to light, which has limited their application.

JP-A-7-196869 proposes compounding zinc oxide into a specific polymer material as antimicrobial agent. However, zinc oxide exhibits small antimicrobial effect so that substantial effects will not be produced unless it is added in a large amount.

Known organic antimicrobial agents include pyrithione and its metal salts, phenols, and organic compounds containing halogen or sulfur.

Although these organic compounds are excellent in antimicrobial properties, many of them are harmful to the human body, and they are insufficient in heat resistance and stability compared with inorganic antimicrobial agents. They tend to decompose or escape from the product to lose their effects when a vinyl chloride resin to which it has been added is heated or on contact with water or oil in use. In such situations, they also produce unfavorable effects such as coloring, generation of smell, and reduction of physical properties of the vinyl chloride resin material. These disadvantages have limited their applicability.

Therefore, it has been keenly demanded to develop an antimicrobial agent that exhibits high heat resistance withstanding the heat processing of polymer materials and high stability against water and oil, undergoes no coloration that would impair commercial value of the product, and has high safety to the human body; and a vinyl chloride resin composition exhibiting excellent antimicrobial properties by addition of the antimicrobial agent.

JP-A-58-1736 discloses use of an aromatic cyclic phosphoric ester metal salt as a nucleating agent for crystalline resins, but effectiveness of the compound as an antimicrobial agent is not described, still less suggested.

DISCLOSURE OF THE INVENTION

Accordingly, an object of the present invention is to provide an antimicrobial composition having excellent antimicrobial properties and fit for medical tools made of a vinyl chloride resin, and a medical tool made of an antimicrobial vinyl chloride resin containing the antimicrobial composition.

As a result of extensive investigation, the present inventors have found that a specific cyclic organic phosphoric ester compound exhibits excellent antimicrobial properties, high heat resistance withstanding the heat processing of a vinyl chloride resin, and stability to water and oil, undergoes no coloration that might ruin the product value, and is highly safe to the human body. The present inventors have continued their study based on this finding and found as a result that a combination of the specific organic acidic phosphoric ester compound and a specific pyrithione compound produces a synergistic effect when added to a vinyl chloride resin and thereby accomplished the above object of the present invention.

The present invention has been completed based on the above findings. The present invention provides an antimicrobial composition for a medical tool made of a vinyl chloride resin, which comprises (a) a cyclic organic phosphoric ester compound represented by formula (I) shown below and (b) a pyrithione compound represented by formula (II) shown below, and a medical tool made of an antimicrobial vinyl chloride resin obtained by adding to a vinyl chloride resin (a) a cyclic organic phosphoric ester compound represented by formula (I) and (b) a pyrithione compound represented by formula (II).

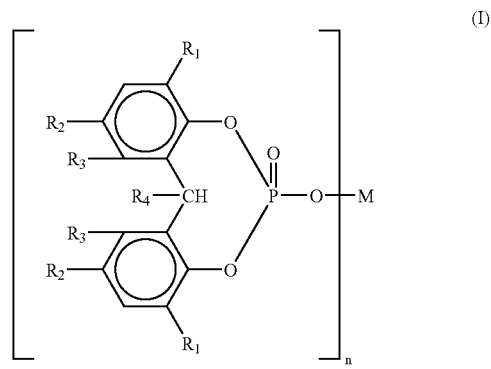

wherein $R_1$, $R_2$, and $R_3$ each represent a hydrogen atom or a straight-chain or branched alkyl group having 1 to 18 carbon atoms; $R_4$ represents a hydrogen atom or a methyl group; n represents 1 or 2; and M represents a hydrogen atom or an alkali metal when n is 1, or an alkaline earth metal or a zinc atom when n is 2.

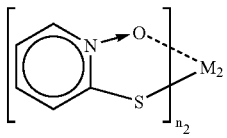

(II)

wherein $M_2$ represents an alkali metal, an alkaline earth metal, a zinc atom, a copper atom or an aluminum atom; and $n_2$ represents the same number as the valence of $M_2$.

BEST MODE FOR CARRYING OUT THE INVENTION

The antimicrobial composition for a medical tool made of a vinyl chloride resin and the medical tool made of an antimicrobial vinyl chloride resin according to the present invention will be described below in detail.

The cyclic organic phosphoric ester compound represented by formula (I) which can be used in the present invention as component (a) is used as an antimicrobial agent that imparts excellent antimicrobial properties to a vinyl chloride resin in cooperation with (b) a pyrithione metal salt represented by formula (II).

In formula (I), the alkyl group represented by $R_1$, $R_2$, and $R_3$ includes methyl, ethyl, propyl, isopropyl, butyl, sec-butyl, tert-butyl, amyl, tert-amyl, hexyl, octyl, 2-ethylhexyl, isooctyl, tert-octyl, nonyl, decyl, dodecyl, tridecyl, isotridecyl, tetradecyl, hexadecyl, and octadecyl.

The alkali metal represented by M includes sodium, potassium, and lithium. The alkaline earth metal includes calcium, magnesium, barium, and strontium. Compounds of formula (I) in which M is an alkali metal or a zinc atom are particularly preferred for their great effects.

Specific examples of the cyclic organic phosphoric ester compound represented by formula (I) include the following compound Nos. 1 to 8.

Compound No. 1:

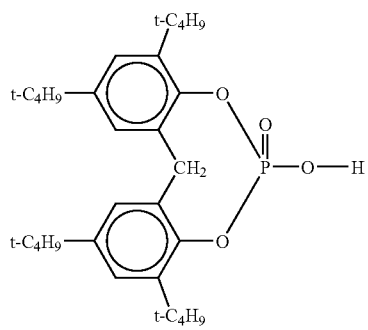

Compound No. 2:

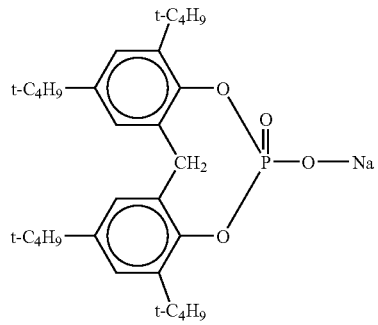

Compound No. 3:

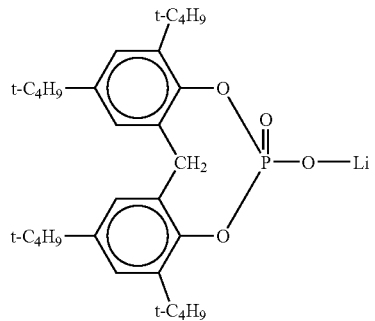

Compound No. 4:

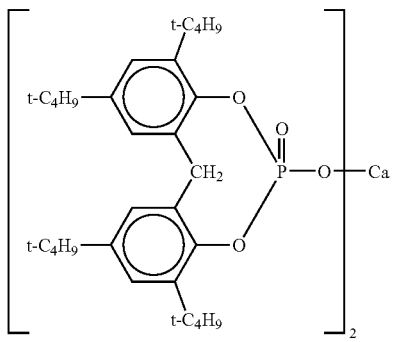

Compound No. 5:

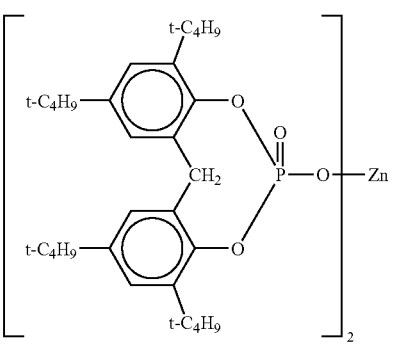

Compound No. 6:

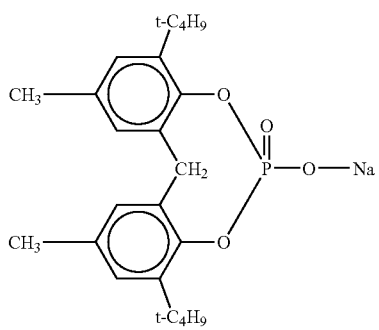

Compound No. 7:

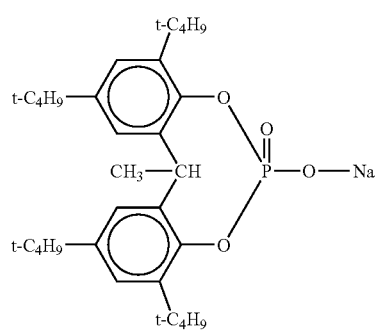

Compound No. 8:

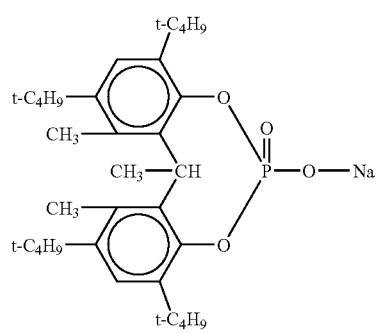

The amount of the cyclic organic phosphoric ester compound to be added is 0.005 to 10 parts by weight, preferably 0.01 to 5 parts by weight, per 100 parts by weight of a vinyl chloride resin. Addition of less than 0.005 parts by weight results in insufficient antimicrobial effects. Addition of more than 10 parts by weight does not lead to appreciable improvement only to result in bad economy.

Because the cyclic organic phosphoric ester compound has excellent stability and satisfactory dispersibility in a vinyl chloride resin, it can be added to a vinyl chloride resin in a powder form. If necessary, it may be used as supported on various carriers or dispersed in a solvent or a liquid additive.

The metal species of the pyrithione compound which can be used as component (b) in the present invention includes alkali metals, alkaline earth metals, zinc, copper, and aluminum. A zinc salt is preferred for its particularly excellent antimicrobial properties. The amount of the pyrithione compound to be added is preferably 0.001 to 0.1 part by weight, still preferably 0.005 to 0.05 parts by weight, per 100 part by weight of a vinyl chloride resin. An amount less than 0.001 part by weight fails to manifest sufficient antimicrobial properties. An amount more than 0.1 part by weight results in unfavorable coloration.

Component (b) is preferably used in an amount of 0.1 to 20 parts by weight per 100 parts by weight of component (a). Out of this compounding ratio, the antimicrobial agent should be added to a vinyl chloride resin in an increased amount in order to achieve sufficient antimicrobial performance over a broad antimicrobial spectrum, which is impractical, resulting in reduction of physical properties of the resin, loss of a commercial value due to coloration, and reduction in hygiene.

The medical tool made of the antimicrobial vinyl chloride resin containing components (a) and (b) according to the present invention can be obtained by adding, to a vinyl chloride resin, the components (a) and (b) either as a mixture thereof in the form of an antimicrobial composition or separately. It is advisable to previously compounding the components (a) and (b) into an antimicrobial composition. If added separately, the components may not be dispersed sufficiently because for one thing the amounts of the antimicrobial components to be added are small. For another, the processing temperature of a vinyl chloride resin is up to 200° C., which is lower for a resin. Previous compounding will make metering easier and help them manifest their antimicrobial properties uniformly.

The medical tool made of the antimicrobial vinyl chloride resin is produced by preparing the antimicrobial vinyl chloride resin in a usual manner and processing the resin into antimicrobial molded articles including films, sheets, bags, tubes, and other shapes by any known method such as extrusion, calendering, injection molding, and press forming. The antimicrobial molded articles are used as antimicrobial vinyl chloride resin-made medical equipment including urologic disposable devices, such as urine bags, urine meters, discrete catheters, Foley catheters, and male external catheters, respiratory organs related devices, and vent line control related devices.

In addition to the cyclic organic phosphoric ester compound of formula (I) and the pyrithione compound of formula (II), the antimicrobial vinyl chloride resin-made medical tool of the present invention can further contain additives commonly used in vinyl chloride resins in amounts that do not impair the effects of the present invention.

Examples of the additives are antioxidants including oxides or hydroxides of alkaline earth metals or zinc and phenol-, phosphorus- or sulfur-based antioxidants, metal soap stabilizers, metal alkylphosphate stabilizers, inorganic metal salt stabilizers, perchlorate compounds, organotin stabilizers, polyol compounds, β-diketone compounds, epoxy compounds, plasticizers, blowing agents, ultraviolet absorbers, hindered amine light stabilizers, fillers, coloring agents, pigments, crosslinking agents, antistatics, antifoggants, lubricants, processing aids, and flame retardants. These additives may be added either separately or as a mixture thereof to a vinyl chloride resin.

The oxides or hydroxides of alkaline earth metals or zinc include those of calcium, magnesium, barium, strontium or zinc. Calcium hydroxide and zinc oxide are particularly preferred for their antimicrobial effects and the effect of improving heat stability of a vinyl chloride resin.

The amount of the alkaline earth metal or zinc oxide or hydroxide to be added is 0.005 to 10 parts by weight, preferably 0.01 to 5 parts by weight, per 100 parts by weight of a vinyl chloride resin. Amounts less than 0.005 parts by weight are insufficient for obtaining satisfactory antimicrobial effects. Amounts exceeding 10 parts by weight bring about little proportionate improvement but rather give adverse influences on the characteristics of the vinyl chloride resin.

The alkaline earth metal or zinc oxide or hydroxide is preferably used in powder form for dispersibility in a polymeric material. A preferred particle size, while not particularly limited, is 0.1 to 100 μm in order not to reduce the characteristics of the vinyl chloride resin. When the powder is added to the vinyl chloride resin, it can be added as such or, if necessary, as a dispersion or paste with a solvent or a liquid additive.

Examples of the phenol-based antioxidants are 2,6-di-t-butyl-p-cresol, stearyl (3,5-di-t-butyl-4-hydroxyphenyl)propionate, thiodiethylenebis[(3,5-di-t-butyl-4-hydroxyphenyl)propionate], triethylene glycol bis[(3-t-butyl-4-hydroxy-5-emthylphenyl)propionate], 3,9-bis [(1,1-dimethyl-2-hydroxyethyl)-2,4,8,10-tetraoxaspiro[5.5]undecane]bis[(3-t-butyl-4-hydroxy-5-methylphenyl)propionate], 4,4'-thiobis (6-t-butyl-m-cresol), 4,4'-butylidenebis(6-t-butyl-m-cresol), 2,2'-methylenebis(6-t-butyl-p-cresol), 2-t-butyl-4-methyl-6-(2-acryloyloxy-3-t-butyl-5-methylbenzyl)phenol, 2,2'-ethylidenebis(4,6-di-t-butylphenyol), 1,1,3-tris(2-methyl-4-hydroxy-5-t-butylphenyl)butane, 1,3,5-tris(2,6-di-t-butyl-4-hydroxybenzyl) isocyanurate, 1,3,5-tris(2,6-dimethyl-3-hydroxy-4-t-butylbenzyl) isocyanurate, 1,3,5-tris(2,6-di-t-butyl-4-hydroxybenzyl)-2,4,6-trimethylbenzene, and pentaerythritol tetra(3,5-di-t-butyl-4-hydroxyphenyl)propionate.

Examples of the phosphorus-based antioxidants are triphenyl phosphite, tris(2,4-di-t-butylphenyl) phosphite, tris(nonylphenyl) phosphite, tris(mixed mono- and dinonylphenyl) phosphite, diphenyl acid phosphite, diphenyl decyl phosphite, phenyl didecyl phosphite, tridecyl phosphite, 2,2'-methylenebis(4,6-di-t-butylphenyl)octyl phosphite, bis (2,4-di-t-butylphenyl)pentaerythritol diphosphite, bis(2,4-dicumylphenyl)pentaerythritol diphosphite, bis(2,6-di-t-butyl-4-methylphenyl)pentaerythritol diphosphite, bis(2,4,6-tri-t-butylphenyl)pentaerythritol diphosphite, tetra($C_{12-15}$ mixed alkyl)bisphenol A diphosphite, tetra(tridecyl)-4,4'-butylidenebis(2-t-butyl-5-methylphenol) diphosphite, hexa(tridecyl)-1,1,3-tris(2-t-butyl-5-methylphenol)triphosphite, 2-butyl-2-ethylpropylene-2,4,6-tri-t-butylphenyl phosphite, and 9,10-dihydro-9-oxa-10-phosphaphenanthrene 10-oxide.

Examples of the sulfur-based antioxidants are dialkyl dipropionates, such as dilauryl, dimyristyl or distearyl ester of thiodipropionic acid, and polyol esters of β-alkylmercaptopropionic acids, such as pentaerythritol tetra(β-dodecylmercaptopropionate).

The metal soap stabilizers include ortho salts, acid salts, basic salts or perbasic salts of group Ia metals (e.g., sodium, potassium, and lithium), group IIa metals (e.g., calcium, magnesium, barium, and strontium) or group IIb metals (e.g., zinc) with aliphatic or aromatic carboxylic acids. They are usually used as a combination of a group IIa metal salt and a group IIb metal salt.

The aliphatic or aromatic carboxylic acids providing the metal soap stabilizers include caproic acid, caprylic acid, pelargonic acid, 2-ethylhexylic acid, capric acid, neodecanoic acid, undecylic acid, lauric acid, myristic acid, palmitic acid, stearic acid, isostearic acid, 12-hydroxystearic acid, ricinoleic acid, linoleic acid, linolenic acid, oleic acid, arachic acid, behenic acid, brassidic acid; fatty acid mixtures obtained from natural fats and oils, such as animal fatty acids, coconut oil fatty acids, soybean oil fatty acids, and cotton seed oil fatty acids; benzoic acid, toluic acid, ethylbenzoic acid, p-t-butylbenzoic acid, and xylylic acid.

Examples of the metal alkylphosphate stabilizers include mono- and/or dioctylphosphates, mono- and/or dilaurylphosphates, and mono- and/or distearylphosphates of group Ia metals (e.g., sodium and potassium), group IIa metals (e.g., calcium, magnesium, barium, and strontium) or group IIb metals (e.g., zinc).

Examples of the inorganic metal salt stabilizers include oxides or hydroxides of group Ia metals (e.g., sodium and potassium), group IIa metals (e.g., calcium, magnesium, barium, and strontium) or group IIb metals (e.g., zinc); basic inorganic acids salts of these metals, such as carbonates, phosphates, phosphites, silicates, borates, and sulfates; aluminosilicates of these metals which have a zeolite crystal structure; and hydrotalcite-like compounds represented by formula:

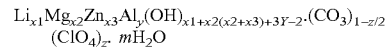

$$Li_{x1}Mg_{x2}Zn_{x3}Al_y(OH)_{x1+x2(x2+x3)+3Y-2} \cdot (CO_3)_{1-z/2} (ClO_4)_z \cdot mH_2O$$

wherein x1, x2, x3, y, and z each represent a number defined below; and m represents 0 or an arbitrary positive number; $0 \leq x1 \leq 10$, $0 \leq x2 \leq 10$, $0 \leq x3 \leq 10$, $1 \leq y \leq 10$, $0 \leq z \leq 1$, and $0 < x1+x2$.

The perchlorate compounds include perchlorates of metals (e.g., sodium, potassium, calcium, magnesium, barium, strontium, and zinc), ammonia or organic amines; and inorganic porous substances having adsorbed perchloric acid.

The organotin stabilizers include carboxylates, mercaptides, and sulfides of mono- and/or dialkyltins, e.g., mono- and/or dimethyltin, mono- and/or dibutyltin, mono- and/or dioctyltin.

Examples of the polyol compounds are glycerol, trimethylolpropane, pentaerythritol, ditrimethylolpropane, dipentaerythritol, sorbitol, mannitol, tris(2-hydroxyethyl) isocyanurate, and their partial esters with aliphatic or aromatic mono- or polycarboxylic acids.

The β-diketone compounds include benzoylacetone, benzoyl pivaloyl methane, benzoyl palmitoyl methane, benzoyl stearoyl methane, dibenzoylmethane, di-t-butylbenzoylmethane, and benzoylcyclohexanone; and complexes of these diketones with a metal, e.g., zinc, calcium or magnesium.

The epoxy compounds include polyglycidyl ethers of polyhydric phenols, such as bisphenol A diglycidyl ether and novolak polyglycidyl ether; alicyclic epoxy compounds, such as vinylcyclohexene dioxide and 3,4-epoxycyclohexyl-3,4-epoxycyclohxane carboxylate; epoxidized natural oils, such as epoxidized soybean oil and epoxidized linseed oil; and alkyl esters of epoxidized unsaturated carboxylic acids.

The plasticizers include alkyl esters of aliphatic or aromatic polycarboxylic acids, such as dibutyl phthalate, dioctyl phthalate, didecyl phthalate, trioctyl trimellitate, tetraoctyl pyromellitate, tetraoctylbiphenyl tetracarboxylate, dioctyl adipate, diisononyl adipate, dioctyl sebacate, dioctyl azelate, and trioctyl citrate; phosphoric esters, such as triphenyl phosphate, tricresyl phosphate, and trixylyl phosphate; polyesters obtained by condensing aliphatic or aromatic polycarboxylic acids and glycols and, if desired, blocking the terminal with monohydric alcohols and/or monocarboxylic acids; and chlorinated paraffin.

The blowing agents include azo blowing agents, such as azodicarboxylic acid diamide, azobisisobutyronitrile, diazodiaminobenzene, and diethyl azodicarboxylate; nitroso blowing agents, such as dinitrosopentamethylenetetramine; hydrazide blowing agents, such as benzenesulfonyl hydrazide, p-toluenesulfonyl hydrazide, toluenesulfonyl azide, and bis(benzenesulfonyl hydrazide) ether; semicarbazide blowing agents, such as toluenesulfonyl semicarbazide; and triazine blowing agents, such as trihydrazinotriazine.

The ultraviolet (UV) absorbers include benzotriazole UV absorbers, such as 2-(2-hydroxy-5-methylphenyl)benzotriazole, 2-(2-hydroxy-5-t-octylphenyl)-benzotriazole, 2-(2-hydroxy-3-t-butyl-5-methylphenyl)-5-chlorobenzotriazole, 2-(2-hydroxy-3,5-di-t-butylphenyl)-5-chlorobenzotriazole, 2,2'-methylenebis(4-t-octyl-6-benzotriazolylphenol), and octyl alcohol or polyethylene glycol ester of 2-(2-hydroxy-3-t-butyl-5-carboxyphenyl)benzotriazole; benzophenone UV absorbers, such as 2-hydroxy-4-methoxybenzophenone, 2-hydroxy-4-octoxybenzophenone, and 5,5'-methylenebis(2-hydroxy-4-methoxybenzophenone); and triazine UV absorbers, such as 2-(2-hydroxy-4-hexyloxy)-4,6-diphenyltriazine and 2-(2-hydroxy4-octoxy)-4,6-dixylyltriazine.

Examples of the hindered amine light stabilizers are bis(2,2,6,6-tetramethyl-4-piperidinyl) sebacate, bis(1,2,2,6,6-pentamethyl-4-piperidinyl) sebacate, tetrakis(2,2,6,6-tetramethyl-4-piperidinyl) butanetetracarboxylate, tetrakis(1,2,2,6,6-pentamethyl-4-piperidinyl) butanetetracarboxylate, bis(2,2,6,6-tetramethyl-4-piperidinyl)ditridecyl butanetetracarboxylate, bis(1,2,2,6,6-pentamethyl-4-piperidinyl) ditridecyl butanetetracarboxylate, a polycondensate of butanetetracarboxylic acid, 3,9-bis(1,1-dimethyl-2-hydroxyethyl)-2,4,8,10-tetraoxaspiro[5.5]undecane, and 2,2,6,6-tetramethyl-4-piperidinol or 1,2,2,6,6-pentamethyl-4-piperidinol, a polycondensate of 1-(2-hydroxyethyl)-2,2,6,6-tetramethyl-4-piperidinol and diethyl succinate, a polycondensate of 1,6-bis(2,2,6,6-tetramethyl-4-piperidinylamino)hexane and dibromoethane, a polycondensate of 1,6-bis(2,2,6,6-tetramethyl-4-piperidinylamino)hexane and 2,4-dichloro-6-t-octylaminotriazine, a polycondensate of 1,6-bis(2,2,6,6-tetramethyl-4-piperidinylarnino)hexane and 2,4-dichloro-6-moirpholinotriazine, 1,5,8,12-tetrakis[2,4-bis(N-butyl-N-(2,2,6,6-tetramethyl-4-piperidinyl)amino)-s-triazin-6-yl]-1,5, 8,1 2-tetraazadodecane, 1,5,8,1 2-tetrakis[2,4-bis(N-butyl-N-(1,2,2,6,6-pentamethyl-4-piperidinyl) amino)-s-triazin-6-yl]-1,5,8,12-tetraazadodecane.

Known inorganic and/or organic antibacterial agents or antifungal agents can be used in combination with the composition of the present invention to enhance the effect and/or broaden the antimicrobial spectrum of the composition.

The inorganic antibacterial or antifungal agents include metals capable of imparting antibacterial and/or antifungal properties, such as silver and copper, and their oxides, hydroxides, phosphates, thiosulfates, and silicates, and inorganic compounds having such metals or metal compounds carried thereon. They are exemplified by products commercially sold as silver or copper zeolites, silver zirconium phosphate, silver hydroxyapatite, silver phosphate glass, silver phosphate ceramics, silver calcium phosphate, etc.

The organic antibacterial agents include nitrogen/sulfur-containing ones, bromine-containing ones, nitrogen-containing ones, and others. The organic nitrogen/sulfur-containing antibacterial agents are exemplified by alkylene bisthiocyanate compounds, such as methylene bisthiocyanate; isothiazoline compounds, such as 5-chloro-2-methyl-4-isothiazolin-3-one, 2-octyl-4-isothiazolin-3-one, 4,5-dichloro-2-octyl-4-isothiazolin-3-one, and N-butyl-1,2-benzoisothiazolin-3-one; sulfonamide compounds, such as chloramine T and N,N-dimethyl-N'-(fluorodichloromethylthio)-N'-phenylsulfamide; thiazole compounds, such as 2-(4-thiocyanomethylthio)benzothiazole and 2-mercaptobenzothiazole; 2-(4-thiazolyl)benzimidazole, 3,5-dimethyl-1,3,5-2H-tetrahydrothiadiazine-2-thione, N-(fluorodichloromethylthio)phthalimide, and dithio-2,2'-bis(benzmethylamide). The organic bromine-containing antimicrobial agents include. organic bromonitro compounds, such as 2-bromo-2-nitropropane-1,3-diol, 1,1-dibromo-1-nitro-2-propanol, 2,2-dibromo-2-nitroethanol, 2-bromo-2-nitro-1,3-diacetoxypropane, β-bromo-β-nitrostyrene, and 5-bromo-5-nitro-1,3-dioxane; organic bromocyano compounds, such as 2,2-dibromo-3-cyanopropionamide; bromoacetic acid compounds, such as 1,2-bis(bromoacetoxy)ethane, 1,4-bis(bromoacetoxy)-2-butene, and bromoacetamide; and organic bromosulfone compounds, such as bis(tribromomethyl) sulfone. The organic nitrogen-containing antimicrobial agents include s-triazine compounds, such as hexahydro-1,3,5-triethenyl-s-triazine and hexahydro-1,3,5-tris(2-hydroxyethyl)-s-triazine; halogenated oxime compounds, such as N,4-dihydroxy-o-oxobenzeneethaneimidoyl chloride and α-chloro-o-acetoxybenzaldoxime; chlorinated isocyanuric acid compounds, such as trichloroisocyanurates and sodium dichloroisocyanurate; quaternary anmmonium compounds, such as benzalkonium chloride and decalinium chloride; carbamic acid compounds such as 2-methylcarbonylaminobenzimidazole; imidazole compounds, such as 1-[2'-[(2,4-dichlorophenyl)]-2'-[(2,4-dichlorophenyl)methoxy]ethyl-3-(2-phenylethyl)-1H-imidazolium chloride; amide compounds such as 2-chloroacetamide; amino alcohol compounds, such as N-(2-hydroxypropyl)aminomethanol and 2-(hydroxymethylamino)-ethanol; and nitrile compounds such as 2,4,5,6-tetrachloroisophthialonitrile.

The present invention will now be illustrated in greater detail with reference to Examples, but it should be understood that the invention is not deemed to be limited thereto. Compound Nos. 1 through 8 used in Examples are compounds listed above as the cyclic phosphoric ester compound.

EXAMPLE 1

A mixture having the formulation described below was roll kneaded at 170° C. to prepare a sheet, which was pressed at 180° C. for 5 minutes to obtain a 0.5 mm thick soft PVC sheet. A 10 mm×10 mm test piece was cut out of the soft PVC sheet and evaluated for antimicrobial properties against bacteria (Nos. 1 to 5 in Table 1) and fungi (Nos. 6 to 8 in Table 1) in accordance with the respective methods described below. The results obtained are shown in Table 1.

For Bacteria:

The culture solution was applied to the test piece, and the test piece was tightly covered with polyethylene cling film. After cultivation at 35° C. for 2 days, the number of surviving cells was counted and rated based on the following criteria.

A: The survival rate is less than 0.1%.
B: The survival rate is 0.1% or more and less than 1%.
C: The survival rate is 1% or more and less than 10%.
D: The survival rate is 10% or more.

For Fungi:

The test piece was placed at the center of a culture dish, and a common agar medium was poured to thinly cover the test piece. The culture solution was applied to the agar medium and cultivated at 35° C. for 1 week. The growth of the fungus was observed and rated based on the following criteria.

A: No growth on the test piece.
B: The grown fungi covers less than 30% of the test piece's surface area.

C: The grown fungi covers 30% or more and less than 70% of the test piece's surface area.

D: The grown fungi covers 70% or more of the test piece's surface area.

| Formulation: | |
|---|---|
| Polyvinyl chloride | 100 (parts by weight, hereinafter the same) |
| Di-2-ethylhexyl phthalate | 50 |
| Epoxidized soybean oil | 2 |
| Zinc stearate | 0.3 |
| Calcium stearate | 0.2 |
| Zinc pyrithione (ZnPT) | 0.01 |
| Test compound (see Table 1) | 0.3 |

TABLE 1

| | | Microorganism | | | | | | | |
|---|---|---|---|---|---|---|---|---|---|
| | Test Compound | 1 | 2 | 3 | 4 | 5 | 6 | 7 | 8 |
| Comp. Ex. 1-1 | none (no ZnPT) | D | D | D | D | D | D | D | D |
| Comp. Ex. 1-2 | none | C | C | C | C | C | C | C | C |
| Ex. 1-1 | No. 1 | A | A | A | A | A | A | A | A |
| Ex. 1-2 | No. 2 | A | A | A | A | A | A | A | A |
| Ex. 1-3 | No. 3 | A | A | A | A | A | A | A | A |
| Ex. 1-4 | No. 4 | A | A | A | A | A | A | A | A |
| Ex. 1-5 | No. 5 | A | A | A | A | A | A | A | A |
| Ex. 1-6 | No. 6 | A | A | A | A | A | A | A | A |
| Ex. 1-7 | No. 7 | A | A | A | A | A | A | A | A |
| Ex. 1-8 | No. 8 | A | A | A | A | A | A | A | A |

Microorganism:
1: *Staphylococcus aureaus*
2: MRSA
3: *Bacillus subtilis*
4: *Lactobacillus*
5: *Escherichia coli*
6: Trichophyton
7: Brewer's yeast
8: Kurokawa mold

EXAMPLE 2

A mixture having the formulation shown below was roll kneaded at 170° C. to prepare a sheet, which was pressed at 180° C. for 5 minutes to obtain a 0.5 mm thick semi-rigid PVC sheet. A 10 mm×10 mm test piece was cut out of the semi-rigid PVC sheet. Zinc pyrithione and a test compound were previously compounded to prepare an antimicrobial composition in a predetermined ratio to give the formulation. The test piece was tested in the same manner as in Example 1. The results obtained are shown in Table 2.

| Formulation: | |
|---|---|
| Polyvinyl chloride | 100 (parts by weight, hereinafter the same) |
| Di-2-ethylhexyl phthalate | 20 |
| Epoxidized soybean oil | 2 |
| Calcium carbonate | 10 |
| Zinc stearate | 0.5 |
| Synthetic hydrotalcite*[1] | 1.0 |
| Calcium hydroxide | 1.0 |
| Antibacterial composition: | |
| Zinc pyrithione | 0.01 |
| Test compound (see Table 2) | 0.5 |

*[1] $Mg_4Al_2CO_3(OH)_{12} \cdot nH_2O$

TABLE 2

| | | Microorganism | | | | | | | |
|---|---|---|---|---|---|---|---|---|---|
| | Test Compound | 1 | 2 | 3 | 4 | 5 | 6 | 7 | 8 |
| Comp. Ex. 2-1 | none (no ZnPT) | D | D | D | D | D | D | D | D |
| Comp. Ex. 2-2 | none | C | C | C | C | C | C | C | C |
| Ex. 2-1 | No. 1 | A | A | A | A | A | A | A | A |
| Ex. 2-2 | No. 2 | A | A | A | A | A | A | A | A |
| Ex. 2-3 | No. 3 | A | A | A | A | A | A | A | A |
| Ex. 2-4 | No. 4 | A | A | A | A | A | A | A | A |

As shown in Tables 1 and 2, in Comparative Examples 1-1 and 2-1 wherein neither zinc pyrithione nor a test compound was added to the vinyl chloride resin, 10% or more of the bacterial cells before testing survived, and 70% or more of the test piece's surface area was covered with the grown fungus. In Comparative Examples 1-2 and 2-2 wherein zinc pyrithione was added to the vinyl chloride resin, but no test compound was added, 1% or more and less than 10% of the bacterial cells survived, and 30% or more and less than 70% of the test piece's surface area was covered with the grown fungi.

By contrast, in Examples 1-1 to 1-8 and 2-1 to 2-4 wherein both zinc pyrithione and the test compound were added to the vinyl chloride resin, only less than 0.1% of the bacterial cells were able to survive, and the fungi were not at all allowed to grow on the test pieces. It has thus been obviously proved that the combination of these components exhibits excellent antimicrobial properties showing extremely broad antimicrobial spectra at small amounts of addition.

INDUSTRIAL APPLICABILITY

The antimicrobial composition for medical tools made of a vinyl chloride resin exhibits excellent antimicrobial properties and provides, antimicrobial medical tools made of a vinyl chloride resin.

What is claimed is:

1. An antimicrobial composition for a medical tool made of a vinyl chloride resin, which comprises (a) a cyclic organic phosphoric ester compound represented by formula (I):

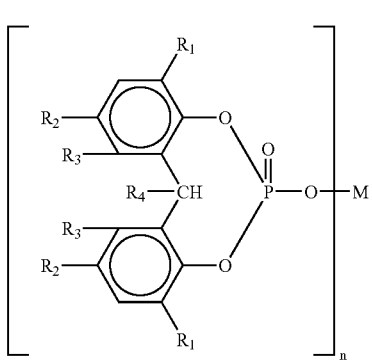

(I)

wherein $R_1$, $R_2$, and $R_3$ each represent a hydrogen atom or a straight-chain or branched alkyl group having 1 to 18 carbon atoms; $R_4$ represents a hydrogen atom or a methyl group; n represents 1 or 2; and M represents a hydrogen atom or an alkali metal when n is 1, or an alkaline earth metal or a zinc atom when n is 2;

(b) a pyrithione compound represented by formula (II):

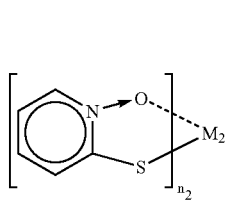

(II)

wherein $M_2$ represents an alkali metal, an alkaline earth metal, a zinc atom, a copper atom or an aluminum atom; and $n_2$ represents the same number as the valence of $M_2$; and wherein component (a) is present in an amount of 0.005 to 10 parts by weight per 100 parts by weight of the vinyl chloride resin; and component (b) is present in an amount of 0.001 to 0.1 part by weight per 100 parts by weight of the vinyl chloride resin.

2. The antimicrobial composition for a medical tool made of a vinyl chloride resin according to claim 1, wherein component (b) is present in an amount of 0.1 to 20 parts by weight per 100 parts by weight of component (a).

3. The antimicrobial composition for a medical tool made of a vinyl chloride resin according to claim 1, wherein M in formula (I) is an alkali metal or a zinc atom.

4. The antimicrobial composition for a medical tool made of a vinyl chloride resin according to claim 1, wherein $M_2$ in formula (II) is a zinc atom.

5. A medical tool made of an antimicrobial vinyl chloride resin having incorporated therein an antimicrobial composition according to claim 1.

6. A medical tool made of an antimicrobial vinyl chloride resin having incorporated therein (a) a cyclic organic phosphoric ester compound represented by formula (I):

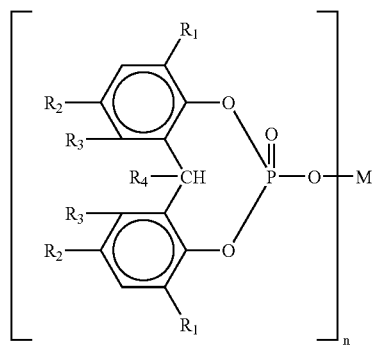

(I)

wherein $R_1$, $R_2$, and $R_3$ each represent a hydrogen atom or a straight-chain or branched alkyl group having 1 to 18 carbon atoms; $R_4$ represents a hydrogen atom or a methyl group; n represents 1 or 2; and M represents a hydrogen atom or an alkali metal when n is 1, or an alkaline earth metal or a zinc atom when n is 2;

(b) a pyrithione compound represented by formula (II):

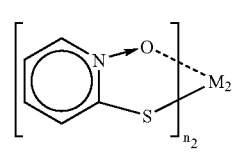

(II)

wherein $M_2$ represents an alkali metal, an alkaline earth metal, a zinc atom, a copper atom or an aluminum atom; and $n_2$ represents the same number as the valence of $M_2$; and wherein component (a) is present in an amount of 0.005 to 10 parts by weight per 100 parts by weight of the vinyl chloride resin; and component (b) is present in an amount of 0.001 to 0.1 part by weight per 100 parts by weight of the vinyl chloride resin.

7. The medical tool made of an antimicrobial vinyl chloride resin according to claim 5, which is a disposable tool.

8. The medical tool made of an antimicrobial vinyl chloride resin according to claim 7, wherein the disposable tool is a urine bag.

9. The antimicrobial composition for a medical tool made of a vinyl chloride resin according to claim 2, wherein M in formula (I) is an alkali metal or a zinc atom.

10. The antimicrobial composition for a medical tool made of a vinyl chloride resin according to claim 2, wherein $M_2$ in formula (II) is a zinc atom.

11. The antimicrobial composition for a medical tool made of a vinyl chloride resin according to claim 3, wherein $M_2$ in formula (II) is a zinc atom.

12. A medical tool made of an antimicrobial vinyl chloride resin having incorporated therein an antimicrobial composition according to claim 2.

13. A medical tool made of an antimicrobial vinyl chloride resin having incorporated therein an antimicrobial composition according to claim 3.

14. A medical tool made of an antimicrobial vinyl chloride resin having incorporated therein an antimicrobial composition according to claim 4.

15. The medical tool made of an antimicrobial vinyl chloride resin according to claim 6, which is a disposable tool.

* * * * *